(12) United States Patent
Grushin et al.

(10) Patent No.: US 6,548,698 B1
(45) Date of Patent: Apr. 15, 2003

(54) OXIDATIVE CARBONYLATION OF TOLUENE CATALYZED BY RHODIUM AND IRIDIUM

(75) Inventors: Vladimir Grushin, Hockessin, DE (US); David Lincoln Thorn, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/604,565

(22) Filed: Jun. 27, 2000

Related U.S. Application Data

(60) Provisional application No. 60/145,126, filed on Jul. 22, 1999.

(51) Int. Cl.[7] .............................................. C07C 51/16
(52) U.S. Cl. ...................... 562/407; 562/408; 562/406; 562/409
(58) Field of Search ................... 562/406, 423, 562/409, 493, 407, 408; 502/153, 161

(56) References Cited

U.S. PATENT DOCUMENTS

| | | | |
|---|---|---|---|
| 3,700,729 A | * 10/1972 | Fenton et al. | |
| 4,356,318 A | 10/1982 | Waller | 562/406 |
| 4,416,801 A | 11/1983 | Waller | 502/153 |
| 4,431,839 A | 2/1984 | Waller | 562/406 |
| 4,463,103 A | 7/1984 | Waller | 502/159 |

FOREIGN PATENT DOCUMENTS

| | | |
|---|---|---|
| FR | 1519934 | 2/1968 |
| GB | 1164561 | 9/1969 |

OTHER PUBLICATIONS

Kalinovskii et al, translated from Zhurnal Obshchei Khimii, vol. 60, No. 1, pp. 123–130, Jan., 1990.*
Taniguchi et al , Chemistry Letters, 1995, pp. 345–346.*
Carey F. A., Organic Chemistry, second edition, 1992, McGraw–Hill, Inc., p. 816).*
Jintoku, Tetsuro et al., Palladium–catalyzed synthesis of aromatic acids from carbon monoxide and aromatic compounds via the aromatic C—H bond activation, *Journal of Organometallic Chemistry*, 385, 297–306, 1990.
Waller, F.J., Catalysis with Metal Cation–Exchanged Resins, *Catal. Rev. –Sci. Eng.*, 28(1), 1–12, 1986.
Fujiwara, Y., Exploitation of Synthetic Reactions via C—H Bond Activation by Transition Metal Catalysts. Carboxylation and Aminomethylation of Alkanes or Arenes, *Synlett*, 591–599, Nov. 1, 1995.
Fujiwara, Yuzo et al., Palladium–promoted One–step Carboxylation of Aromatic Compounds with Carbon Monoxide, *J.C.S. Chem. Comm.*, 220–221, 1980.
Fujiwara, Yuzo et al., Palladium–promoted One–step Synthesis of Aromatic Acid Anhydrides from Aromatic Compounds with Carbon Monoxide, *J. Chem. Soc., Chem. Commun.*, 132–133, 1982.
Fujiwara, Yuzo et al., Palladium–Catalyzed One–Step Synthesis of Aromatic Acids from Aromatic Compounds with Carbon Monoxide, *Journal of Organometallic Chemistry*, 256, C35–C36, 1983.
Ugo, Renato et al., Catalysis by Palladium Salts. Part 2. Palladium–catalysed Carboxylation with Carbon Monoxide of Aromatic Compounds Working under Mild Conditions, *J. Chem. Soc. Perkin Trans. 1*, 2625–2629, 1987.
Taniguchi, Yuki et al., Palladium (II) Catalyzed Carboxylation of Aromatic Compounds with CO under Very Mild Conditions, *Chemistry Letters 1995*, 345–346, 1985.
Kalinovskii, I.O. et al., Oxidative Carbonylation of Benzene Derivatives in the Presence of Rhodium, Palladium, and Copper Compounds, UDC 546.262.31+546.21:547.53, *Plenum Publishing Corporation*, 108–113, 1990.
Gol'dshleger, N.F. et al., Rhodium (II) Trifluoroacetate, UDC 542.91:547.464.2'161–38:546:973, *Plenum Publishing Corporation*, 238, 1991.

* cited by examiner

*Primary Examiner*—Samuel Barts

(57) ABSTRACT

This invention relates generally to the oxidative carbonylation of toluene, catalyzed by rhodium or iridium complexes in the presence of an oxidant and under mild conditions, whereby toluic acid is produced with para-selectivity up to 98%.

23 Claims, No Drawings they both can be used. An example of strong acid medium includes, but is not limited

OXIDATIVE CARBONYLATION OF TOLUENE CATALYZED BY RHODIUM AND IRIDIUM

This application claims the benefit of Provisional Application Ser. No. 60/145,126 filed Jul. 22, 1999.

FIELD OF THE INVENTION

This invention relates generally to the oxidative carbonylation of toluene, catalyzed by rhodium complexes in the presence of an oxidant, whereby para-toluic acid is produced at selectivities over 90%, or by iridium complexes wherein para-toluic acid is produced at somewhat lower selectivities.

TECHNICAL BACKGROUND OF THE INVENTION

The oxidative carbonylation reaction of aromatic compounds is an attractive method for the direct synthesis of aromatic carboxylic acids from arenes and carbon monoxide. In particular, oxidative carbonylation of toluene produces toluic acids that can be oxidized for manufacturing phthalic, isophthalic, and terephthalic acids employed as monomers for polyesters.

As used herein, "turnover number" (TON) means the number of molecules transformed per catalyst molecule. Higher TON's in comparable times indicate higher catalyst efficiency.

Palladium catalysts in the presence of oxidants (see, for example: Fujiwara, Y.; Kawata, I.; Sugimoto, H.; Taniguchi, H., J. Organomet. Chem. 1983, 256, C35; Jintoku, T.; Fujiwara, Y.; Kawata, I.; Kawauchi, T.; Taniguchi, H., J. Organomet. Chem. 1990, 385, 297; Ugo, R.; Chiesa, A., J. Chem. Soc., Perkin Trans. I 1987, 2625; Taniguchi, Y.; Yamaoka, Y.; Nakata, K.; Takaki, K.; Fujiwara, Y., Chem. Lett. 1995, 345) have been used, but the catalytic turnover numbers (TON) achieved for the carbonylation of toluene were low (2–8). Additionally, the para-selectivity of the reaction never exceeded 67%, normally being in the range of 40 to 55%. The TON's were increased when oxygen was used as the oxidant in the presence of a cuprous promoter, but the para-selectivity was still relatively low (about 46%).

J. J. Van Venrooy, U.S. Pat. No. 4,093,647, reported carbonylation of toluene using palladium catalyst with thallium, which was added in stoichiometric amounts and improved para-selectivity.

Rhodium catalysts have also been used for the oxidative carbonylation of toluene, improving the para-selectivity to between 63 and 94% (see, for example: Kalinovskii, I. O.; Lescheva, A. A.; Kuteinikova, M. M.; Gel'bshtein, A. I. Zh. Obshch. Khim. 1990, 60, 123, J. Gen. Chem. USSR 1990, 60, 108 (English Translation)). Relatively good TON's were obtained, but only when the reactions were run at 140° C. using CO and $O_2$ reactants with Cu promoter under pressures of about 150 to 250 psi and in ratios within explosive limits. F. J. Waller, U.S. Pat. Nos. 4,356,318; 4,416,801; 4,431,839; 4,463,103 to DuPont, and F. J. Waller, Catal. Rev. Sci. Eng. 1986, 28, 1, reported the carbonylation of toluene catalyzed with perfluorinated ion-exchange polymer/Rh composite occurring under more severe conditions, 150° C. and 2000–4000 psi of CO containing 3% $O_2$. Although the $CO/O_2$ ratio was outside explosive limits, the TON's achieved were low (<9). Running the reaction in the presence of $Cu^{2+}$, triflic acid and triflic anhydride resulted in slightly higher TON's (42), the reaction conditions required still being relatively drastic.

The rhodium-catalyzed process described by Kalinovskii et al., Zh. Obshch. Khim. 1990, 60, 123, J. Gen. Chem. USSR 1990, 60, 108 (English Translation); Kalinovskii, I. O.; Lescheva, A. A.; Pogorelov, V. V.; Gel'bshtein, A. I., Khim. Tverd. Topliva 1993, 8, gives substantial quantities of hydroxylated side-products when water is present in the reaction mixture.

SUMMARY OF THE INVENTION

The present invention discloses a para-selective process for preparing toluic acid, comprising: combining toluene, carbon monoxide, having a pressure from about 0 and about 5000 psi, and an oxidant, with a rhodium catalyst, in an acid medium.

The present invention also discloses a para-selective process for preparing toluic acid, comprising: combining toluene, carbon monoxide, and an oxidant, with an iridium catalyst, in an acid medium.

Another disclosure of this invention is a process for preparing a mixture of p-toluic and m-toluic acids, comprising: combining toluene, carbon monoxide, and an oxidant, under oxidizing conditions, with a suitable rhodium or an iridium catalyst, in an acid medium, wherein the mixture of p-toluic and m-toluic acids may be oxidized to make terephthalic and isophthalic acids suitable for use, without separation, in the formation of polyester materials.

DETAILED DESCRIPTION OF THE INVENTION

This invention relates to a process for the selective catalytic synthesis of para-toluic acid by reacting toluene in the presence of carbon monoxide (CO) and an oxidant in strong acid medium and in the presence of a rhodium catalyst. Examples of oxidants include, but are not limited to $K_2S_2O_8$, oxygen and air, which by definition comprises oxygen. Although $K_2S_2O_8$ is a preferred persulfate, other persulfates of the formula $M_xM'_yS_2O_8 \cdot zH_2O$ can be used. An example of strong acid medium includes, but is not limited to, trifluoroacetic acid. In the formula $M_xM'_yS_2O_8 \cdot zH_2O$, M and M' are cations selected from the group consisting of Li, Na, K, Rb, Cs, and H, x+y=2, and z is any number from 0 to about 10. If $K_2S_2O_8$ is used the process can be carried out at temperatures that are about or slightly above room temperature. The desired p-toluic acid is produced at greater than 90% selectivity. If oxygen gas ($O_2$) or air is used the process can be carried out at temperatures up to about 120° C. or above with $CO/O_2$ or CO/air ratios below the explosive limit. The desired p-toluic acid is produced in about or above 65% selectivity. By either method, the p-toluic acid produced may subsequently be used to make terephthalic acid. The terephthalic acid can be used as a monomer in a variety of polymerization reactions, including the production of polyesters.

When $O_2$ or air is used as the oxidant and the reaction is run at elevated temperatures for example, at about 120° C. or above, significant amounts of m-toluic acid are formed in addition to the p-toluic acid. This mixture of p- and m-toluic acids may be used subsequently to make mixed terephthalic and isophthalic acids, which can be used for making polyester materials.

This invention also relates to a process for the selective catalytic synthesis of para-toluic acid by reacting toluene in the presence of carbon monoxide (CO) and an oxidant (for example, $K_2S_2O_8$, oxygen or air) in mild acid (for example, acetic acid) medium in the presence of an iridium catalyst. If $K_2S_2O_8$ is used the process can be can be carried out at temperatures at or above about 100° C. When iridium catalyst is used the para-selectivity is generally less than about 80% selectivity, which is lower than that observed for rhodium catalyst. Any iridium compound capable of dissolving in the reaction medium under the reaction conditions described is suitable. Specific compounds are described below. Mixtures of p- and m-toluic acids may also be formed using these iridium catalysts, and, as described above, may be used to make mixed terephthalic and isophthalic acids, which in turn can be used for making polyester materials.

Reaction Media:

A mixture of trifluoroacetic acid and toluene is used as the reaction medium. Although other fluorinated carboxylic acids can be used (e.g., perfluorobutyric acid) trifluoroacetic acid was used mostly in the examples below. The trifluoroacetic acid:toluene ratio may vary in a broad range. Most experiments using $K_2S_2O_8$ oxidant and rhodium catalyst were carried out in 1:1, volume/volume (v/v) trifluoroacetic acid:toluene. When oxygen gas or air is used as the oxidant with rhodium catalyst the trifluoroacetic acid:toluene ratio is smaller, from as little as about 1:100 up to about 1:5 (v/v), and the addition of trifluoroacetic anhydride results in improved yield of toluic acids.

When $K_2S_2O_8$ is used as the oxidant, the reaction readily occurred in the presence of small amounts of water, although evidence has been obtained for the water gas shift reaction taking place when $H_2O$ is present. When water was present in small amounts no significant formation of cresols (side products) took place, in contrast with the substantial quantities of hydroxylated side-products observed when water was present in the rhodium-catalyzed process described by Kalinovskii, I. O.; Lescheva, A. A.; Pogorelov, V. V.; Gel'bshtein, A. I., *Khim. Tverd. Topliva* 1993, 8. We also found that using $K_2S_2O_8$ as an oxidant and rhodium catalyst, very sluggish reactions with poor conversions and yields were observed in the presence of trifluoroacetic anhydride. This was unexpected since the beneficial effect of acid anhydrides (and trifluoroacetic anhydride in particular) had been reported by Kalinovskii et al., Zh. Obshch. Khim. 1990, 60, 123, J. Gen. Chem. USSR 1990, 60, 108 (English Translation).

Reaction Conditions:

When $K_2S_2O_8$ or a related persulfate is used as the oxidant with rhodium catalyst, the most preferred carbon monoxide pressure is around 1 atm. (14 psig to 15 psig). The reaction can be performed under higher carbon monoxide pressure with some decrease in reaction rate, all other factors held constant. The reaction temperature can range from about 0° C. to about 200° C., preferably from about 20° C. to about 100° C., and most preferably from 20° C. to 70° C. It is preferred that the reaction mixture be stirred, most preferred the mixture be magnetically stirred at a rate of from 100 to 1000 rpm.

When air or oxygen is used as the oxidant with rhodium catalyst, the most preferred pressure of oxidant is 1000 psig, and the most preferred pressure of carbon monoxide is 120 psig. The reaction temperature in this case can range from about 0° C. to about 300° C., preferably from about 50° C. to about 300° C., and most preferably from about 100° C. to about 200° C. When $K_2S_2O_8$ or a related persulfate is used as the oxidant with iridium catalyst, the most preferred carbon monoxide pressure is around 1 atm. (14 to 15 psig). The most preferred temperature range is from about 90° C. to about 120° C.

Other oxidants that are useful in this invention include hydrogen peroxide and trifluoroperacetic acid. Trifluoroperacetic acid is naturally generated in mixtures of hydrogen peroxide and trifluoroacetic acid or anhydride.

Catalysts:

Solutions of rhodium (III) oxide in trifluoroacetic acid are active catalysts. These solutions are obtained by dissolving commercially obtained rhodium (III) oxide in trifluoroacetic acid containing small amounts of water. This catalyst has not been previously reported for oxidative carbonylation reactions. Similar catalyst solutions are obtained by dissolving hydrated rhodium oxide, freshly precipitated from aqueous solutions of $RhCl_3$ as in Example 4(a) below, in trifluoroacetic acid. Limited amounts of Cl (1 mole per mole Rh) do not deactivate the catalyst. Commercial samples of "$RhCl_3.nH_2O$" are initially inactive but after a relatively long period of time (about 1 day at room temperature) under the reaction conditions (trifluoroacetic acid, toluene, CO, $K_2S_2O_8$) catalytically active species are produced, which can successfully catalyze the reaction. Solutions of the carbonyl complex $[(CO)_2Rh(trifluoroacetate)]_n$ also result in active catalysis under the reaction conditions, and solutions of the carbonyl complex $[(CO)_2Rh(trifluoroacetate)]_n$ after treatment with oxidizing agents (for example hydrogen peroxide) also serve as active catalysts. Other carbonyl complexes $[(CO)_2RhX]n$ (X is an anionic ligand selected from the group consisting of acetylacetonate, trifluoroacetylacetonate, hexafluoroacetylacetonate, formate, acetate, benzoate, toluate, trifluoroacetate, nitrate, sulfate, phosphate, trifluoromethanesulfonate, carbonate, fluoride, chloride, bromide, iodide, methoxide, ethoxide, i-propoxide, n-propoxide, n-butoxide, sec-butoxide, and t-butoxide) also serve as catalyst precursors. Other rhodium complexes, for example $(PPh_3)_3RhCl$, may serve as catalyst precursors, although the phosphine ligand is not necessary for catalysis.

Iridium catalysts can also be used as stated above. The iridium catalyst is generated by a process which combines the reaction medium with an iridium compound from the group $IrY_3.nH_2O$ where n is any number between 0 and about 10, and where Y is an anion selected from the group consisting of fluoride, chloride, bromide, and iodide. The iridium catalyst may also be generated by a process which combines the reaction medium with an iridium compound from the group $IrY'(CO)_yL_z$, where L is a neutral ligand selected from the group consisting of triphenylphosphine, pyridine, methylpyridine, aniline, and toluidine, and for y and z being any numbers such that y+z=2 or 3, and where Y' is an anion from the group fluoride, chloride, bromide, iodide, formate, acetate, propionate, carbonate, nitrate, phosphate, sulfate, trifluoroacetate, cyclopentadienide, and pentamethylcyclopentadienide.

Oxidant:

Suitable oxidants include, but are not limited to oxygen gas, air, and peroxodisulfate, $K_2S_2O_8$. When potassium $K_2S_2O_8$, was used as the oxidant with rhodium catalyst the reaction occurred under very mild conditions (about 20° C. to about 65° C.). This oxidant has been previously used for the reported Pd-catalyzed oxidative carbonylation of aromatics with poor TON's and selectivities. The use of this oxidant with Rh catalysts is novel.

When oxygen or air was used as the oxidant with rhodium catalyst the reaction required higher temperature to achieve significant rates, up to at least 200° C. In contrast to previous reports (Kalinovskii et al., Zh. Obshch. Khim. 1990, 60, 123, J. Gen. Chem. USSR 1990, 60, 108 (English Translation); Kalinovskii, I. O.; Lescheva, A. A.; Pogorelov, V. V.; Gel'bshtein, A. I., Khim. Tverd Topliva 1993, 8) the process works with a $CO/O_2$ ratio or CO/air ratio that is lower than the explosive limit.

Process Conditions and para-Selectivity:

Using $K_2S_2O_8$ oxidant and rhodium catalyst, the catalytic reaction readily occurs at 1 atm. of CO and at 20° C. to 65° C. to produce toluic acid with 90–98% para-selectivity, the rest of the toluic acid being m-toluic acid. The highest selectivity was observed when the process was run at room temperature. The only side products detected by GC-MS were isomeric bitolyls (1–5% yield). In contrast, all previously reported Rh-catalyzed oxidative carbonylation reactions required temperatures above 140° C. and PCo= 200–4000 psi.

In some of the examples described below, the p-toluic acid produced in the reaction was not isolated; its yield was determined by GC-MS analysis with chlorobenzene as an internal standard. The instrument used was a Hewlett-Packard 6890 GC/MS instrument with a commercially-supplied 2.5 m×0.25 mm ID capillary column packed with Chromopack #7717 CP-wax 58 (FFAP) CB and modified with nitroterephthalic acid and bonded with polyethylene glycol.

EXAMPLES

Unless otherwise noted, all chemicals and reagents were used as received from Aldrich Chemical Co., Milwaukee, Wis.

Example 1

Synthesis of $[Rh(CO)_2(trifluoroacetate)]$

Trifluoroacetic acid (0.20 mL) was added, in air, to a hot solution of $[(acetylacetonate)Rh(CO)_2]$ (prepared as described in: Varshavskii, Yu. S.; Cherkasova, T. G., *Russ. J. Inorg. Chem.* 1967, 12, 899) (0.364 g) in hexanes (12 mL). The mixture turned dark and golden crystals of $[Rh(CO)_2(trifluoroacetate)]$ precipitated immediately. After the mixture was kept in an ice bath for 1 hour, the solid product was separated, washed with hexanes (5×2 mL), and dried under vacuum. The yield was 0.345 g (90%). Anal. Calculated: C, 17.7; H, 0.0; F, 21.0. Found: C, 17.4; H, 0.3; F, 21.0.

Example 2

Trifluoroacetic acid (0.38 mL) was added, in air, to a hot solution of $[(acetylacetonate)Rh(CO)_2]$ (0.50 g) in hexanes (15 mL). The mixture turned dark and golden crystals of $[Rh(CO)_2(trifluoroacetate)]$ precipitated immediately. After the mixture was kept in an ice bath for 1 hour, the solid product was separated, washed with hexanes, and dried under vacuum. The yield was 0.48 g (91%).

Example 3

Catalytic Studies: Oxidative Carbonylation of Toluene Oxidative Carbonylation with Rh(III Trifluoroacetate Catalyst (a) Catalyst Preparation A mixture of "Rhodium (III) oxide hydrate" (Aldrich, catalogue No. 20,629-6;170 mg), water (1 mL), and trifluoroacetic acid (3 mL) was stirred under reflux for 1 day. No solid dissolved. The mixture was transferred to a Fischer-Porter tube equipped with a magnetic stirring bar, the flask was rinsed with trifluoroacetic acid (2×0.5 mL), and the washings were added to the tube. The suspension was stirred at 175° C. (oil bath) for 42 hours until all solids dissolved to produce a red-brown solution. The latter (total volume=2.5 mL) was filtered, leaving only trace amounts of insolubles on the Teflon® membrane. The decrease in the total volume of the solution was obviously due to solvent losses when the mixture was refluxed in an open flask for 1 day.

(b) Reaction

A mixture of $K_2S_2O_8$ (1.35 g), trifluoroacetic acid (5 mL), 0.083 mL of a catalyst solution as prepared in Example 3(a) above, and toluene (5 mL) was stirred under CO (1 atm) at 53° C. (oil bath) for 16 hours. After the reaction was quenched with water, the unreacted toluene was removed with an air flow over the liquid phase. Ether (20 mL) and chlorobenzene (internal standard; 0.15 mL) were added. After vigorously stirring the mixture for 5–10 minutes, the ethereal phase was analyzed by GC-MS. The GC yield of toluic acid was 260 mg (TON=58, assuming that the Rh oxide used to prepare the catalyst contained 5 molecules of water per each $Rh_2O_3$ unit). The ether layer was separated, and the aqueous layer was extracted with ether. The combined ether solutions were evaporated to dryness to give solid toluic acid which was purified by vacuum sublimation. The yield of the purified toluic acid ($^1$H NMR: 95% p-isomer) was 222 mg.

Example 4

Catalyst Concentration Effect (a) Catalyst Preparation

A solution of NaOH (1.9 g) in water (20 mL) was added to a solution of $RhCl_3 \cdot nH_2O$ (1.01 g) in water (20 mL). As the alkali was being added, a precipitate first formed, and subsequently dissolved. After 45 minutes, acetic acid was added dropwise, causing precipitation of a yellow solid which then partly dissolved after a total of 3 mL of acetic acid was added. To re-precipitate the solid with less losses, the suspension was treated with NaOH until the solid dissolved and a slightly cloudy orange solution formed. The latter did not clear upon addition of another 2 g of NaOH. This solution was neutralized with acetic acid again, now to pH=6. The precipitate was filtered off, washed with water, and dried on the filter. No vacuum drying was applied to ensure solubility of the product in trifluoroacetic acid. The very wet product (1.40 g) easily and completely dissolved in 10 mL of trifluoroacetic acid, at room temperature, to form the active catalyst solution.

On the following day, the acidified (to pH=6) mother liquor released a fine yellow solid which was filtered off, washed with water, and dried. The yield of this solid (insoluble in trifluoroacetic acid) was 366 mg. Assuming that (i) this precipitate is $Rh_2O_3 \cdot nH_2O$, where n=ca. 5 (Strem catalogue of chemicals), (ii) the rest of Rh ended up in the trifluoroacetic acid solution, with virtually no losses, and (iii) the rhodium chloride used was a trihydrate, one can estimate the amount of Rh in the trifluoroacetic acid solution to be ca. 17 mg/mL.

(b) Concentration Effect

A mixture of $K_2S_2O_8$ (1.35 g), trifluoroacetic acid (4 mL), and the catalyst solution as prepared in Example 4(a) (1 mL) was stirred in air for 10 minutes. After toluene (5 mL) was added, the mixture was stirred under CO (1 atm) at room temperature for 66 hours. The mixture was diluted with water (5 mL), basified with NaOH, washed with ether, acidified with HCl, and thoroughly extracted with ether. The combined etherial extracts were evaporated to dryness. The residue was sublimed under vacuum to give 225 mg (TON=10) of p-toluic acid of >95% purity ($^1$H NMR).

(c) Concentration Effect

In an experiment similar to Example 4(b) above, the amount of the catalyst solution used was decreased by two thirds (to 0.34 mL), other things being equal. The yield of p-toluic acid was 328 mg (TON=44). Further decreasing the amount of the catalyst to 0.1 mL resulted in the formation of 155 mg of p-toluic acid, corresponding to TON=71.

Example 5

Oxidative Carbonylation of Toluene in Presence of p-Toluic Acid

A mixture of $K_2S_2O_8$ (1.40 g), trifluoroacetic acid (5 mL), the catalyst solution prepared as in Example 3(a) (0.083 mL), and toluene (5 mL) was stirred under CO (1 atm) at room temperature for 1 day. Water was added, and the unreacted toluene was removed by an air flow. Ether and chlorobenzene (internal standard; 0.1 mL) were added, and the organic layer was analyzed by GC-MS. The GC yield of p-toluic acid was 160 mg (TON=ca. 30). When this run was repeated in the presence of 155 mg of p-toluic acid (easily soluble in trifluoroacetic acid and trifluoroacetic acid/ toluene), the yield of toluic acid was determined to be 335 mg. Therefore, 335–155=180 mg of the acid was produced by the catalytic reaction (TON=ca. 34). This amount is comparable to that obtained in the absence of toluic acid. In both reaction mixtures, small quantities (ca. 1%) of bitolyls were detected. Cresols were not observed.

Example 6

Oxidative Carbonylation of Toluene, Catalyzed by $[Rh(CO_2(trifluoroacetate)]_x$ To a stirring mixture of $K_2S_2O_8$ (1.40 g) and trifluoroacetic acid (5 mL) was added golden-yellow $[Rh(CO)_2(trifluoroacetate)]_x$ (17 mg). The reaction mixture turned deep purple immediately. Toluene (5 mL) was added, and the dark mixture was stirred under CO (1 atm) at 65° C. (oil bath). The color changed first to dark-red and then tan-brown in 0.5 and 2 hours, respectively. After 54 hours water was added to the mixture. The solution was evaporated, and the resulting mixture was extracted with ether (3×20 mL). The combined ether extracts were dried with $MgSO_4$ and taken to dryness, leaving 470 mg of toluic acid (TON=55). The product was determined by proton NMR spectroscopy to be a mixture of p-toluic acid (90–95%) and m-toluic acid (5–10%).

Example 7

$RhCl_3$-Catalyzed Oxidative Carbonylation of Toluene

Trifluoroacetic acid (5 mL) was added to $RhCl_3.nH_2O$ (10 mg). To this suspension (the Rh complex was insoluble), $K_2S_2O_8$ (1.40 g) was added, and the mixture was stirred in air for 15 minutes. After toluene (5 mL) was added, the mixture was stirred under CO for 24 hours, and then analyzed by GC-MS, in a usual manner (see above), with chlorobenzene as an internal standard. No toluic acid formed. When the rhodium chloride-catalyzed reaction was run for 61 hours under similar conditions, about 185 mg of p-toluic acid formed (TON=38).

Example 8

Oxidative Carbonylation of Toluene in the Presence of Air (a) Catalyst Preparation Hydrogen peroxide (30%) was added in 3 portions (0.25 mL each) to a stirring suspension of $[Rh(CO)_2(trifluoroacetate)]$ (300 mg) in TFA (7 mL). The solid dissolved immediately. After gas evolution ceased, the solution was refluxed for about 5 min, until the dark-green color turned orange. After more 30% hydrogen peroxide (0.25 mL) was added the solution was refluxed for 30 min, evaporated, and the residue was dried under vacuum to give an amorphous orange solid. The latter was dissolved in 6.7 mL of TFA. The resulting solution was used as a catalyst for the reaction described below in Example 8(b).

(b) Reaction

A mixture of toluene (5 mL), trifluoroacetic anhydride (1 mL), and the catalyst solution as prepared above (0.3 mL) was pressurized, at room temperature, with air (1000 psig) and CO (120 psig). The resulting mixture was stirred at 200° C. for 2 hours. After the mixture was cooled down to room temperature, the solvents were evaporated. The residue was redissolved in ether and analyzed by GC-MS with chlorobenzene as an internal standard. A mixture of p-toluic acid and m-toluic acid (70:30) was produced with TON=20, along with trace amounts of o-toluic acid.

Example 9

Oxidative Carbonylation of Toluene in the Presence of Ir catalysts in Acetic Acid A mixture of $IrCl_3.nH_2O$ (53.64% Ir; n=ca. 3;17 mg), acetic acid (7 mL), and $K_2S_2O_8$ (1.30 g) was stirred at room temperature for 15 minutes. After toluene (3 mL) was added, the mixture was stirred under CO at 100° C. (oil bath) for 63 hours. Water (40 mL) and ether (10 mL) were added to the mixture at room temperature upon stirring. GC-MS analysis of the ether layer indicated the presence of p-toluic acid, benzaldehyde, and benzyl acetate as three main products and trace amounts of cresols and benzoic acid. A similar result was obtained when $[(p-CH_3C_6H_4NH_2)Ir(CO)_2Cl]$ was used instead of iridium chloride. The toluic acid produced was not isolated. The MS library identified the acid product as p-toluic acid (quality of fit 94%) rather than m-toluic acid (quality of fit ca. 40%).

What is claimed is:

1. A para-selective process for preparing toluic acid, comprising: combining toluene, carbon monoxide having a pressure from about 0 psi to about 5000 psi, and an oxidant selected from the group consisting of $O_2$, air, $M_xM'_yS_2O_8.zH_2O$, where M and M' are cations selected from the group consisting of Li, Na, K, Rb, Cs, and H and wherein x+y=2, and z is any number from 0 to about 10, hydrogen peroxide and trifluoroperacetic acid;

with a rhodium catalyst, in an acid medium and in the absence of a copper promoter.

2. The process of claim 1 wherein the oxidant comprises $K_2S_2O_8$.

3. The process of claim 1 wherein the acid medium is trifluoroacetic acid and wherein water is present in an amount up to about 10% (v/v).

4. The process of any one of claims 1, 2 and 3 wherein said combining is done at temperatures from about 0° C. to about 300° C.

5. The process of any one of claims 1, 2 and 3 wherein toluene is present in an amount greater than about 30% (v/v) and wherein said combining is done at temperatures from about 0° C. to about 300° C.

6. The process of claim 1 further comprising a step of contacting any $[XRh(CO)_2]$ with the acid medium, optionally in the presence of an oxidant selected from the group consisting of $K_2S_2O_8$, $O_2$, air, hydrogen peroxide, and trifluoroperacetic acid, to prepare the rhodium catalyst; wherein X is an anionic ligand selected from the group consisting of acetylacetonate, trifluoroacetylacetonate, hexafluoroacetylacetonate, formate, acetate, benzoate, toluate, trifluoroacetate, nitrate, sulfate, phosphate, trifluoromethanesulfonate, carbonate, fluoride, chloride, bromide, iodide, methoxide, ethoxide, i-propoxide, n-propoxide, n-butoxide, sec-butoxide, and t-butoxide.

7. The process of claim 1 further comprising a step of contacting rhodium oxide with trifluoroacetic acid, at a temperature between about 0° C. and about 200° C., wherein water is present in amounts up to about 80% (v/v), to prepare the rhodium catalyst.

8. The process of claim 1 further comprising a step of contacting hydrated or partially hydrated rhodium trichloride with trifluoroacetic acid, wherein water is present in an amount less than about 10% (v/v); optionally in the presence of one or more of an oxidant, toluene and carbon monoxide, to prepare the rhodium catalyst.

9. The process of claim 1 wherein the oxidant is oxygen or air, and the contacting is done at a temperature of between about 0° C. and about 300° C.

10. The process of claim 1 wherein the acid medium comprises trifluoroacetic acid in an amount greater than zero but less than about 20% (v/v) and wherein said acid medium further comprises trifluoroacetic anhydride in an amount up to about 20% (v/v).

11. A para-selective process for preparing toluic acid, comprising: combining toluene, carbon monoxide, and $M_xM'_yS_2O_8 \cdot zH_2O$, where M and M' are cations selected from the group consisting of Li, Na, K, Rb, Cs, and H and wherein x+y=2, and z is any number from 0 to about 10, with an iridium catalyst, in an acid medium.

12. The process of claim 11 wherein the acid medium is selected from the group consisting of acetic acid and propionic acid, and wherein water is present in an amount up to 10% (v/v).

13. The process of claim 11 wherein the process is carried out a temperature from between about 80° C. and about 200° C., and at a reaction pressure between about 14 psi and about 2000 psi; and further comprising a step of introducing any iridium compound capable of dissolving in the acid medium under said temperature and pressure to generate the iridium catalyst.

14. The process of claim 11 further comprising a step of preparing the iridium catalyst from an iridium compound of the formula $IrX_3 \cdot nH_2O$ wherein n is any number between 0 and about 10, and X is an anion selected from the group consisting of fluoride, chloride, bromide and iodide.

15. The process of claim 11 further comprising a step of preparing the iridium catalyst from an iridium compound of the formula $IrX(CO)_yL_z$ wherein L is a neutral ligand selected from the group consisting of triphenylphosphine, pyridine, methylpyridine, aniline, and toluidine, and wherein y+z=2 or 3, and X is an anion selected from the group consisting of fluoride, chloride, bromide, iodide, formate, acetate, propionate, carbonate, nitrate, phosphate, sulfate, trifluoroacetate, cyclopentadienide, and pentamethylcyclopentadienide.

16. A para-selective process for preparing toluic acid, comprising: combining toluene, carbon monoxide, and an oxidant selected from the group consisting of $O_2$, air, $M_xM'_yS_2O_8 \cdot zH_2O$, where M and M' are cations selected from the group consisting of Li, Na, K, Rb, Cs, and H and wherein x+y=2, and z is any number from 0 to about 10, hydrogen peroxide and trifluoroperacetic acid, with a catalyst consisting essentially of an iridium compound, in an acid medium.

17. The process of claim 16 wherein the acid medium is selected from the group consisting of acetic acid and propionic acid, and wherein water is present in an amount up to 10% (v/v).

18. The process of claim 16 wherein the process is carried out a temperature from between about 80° C. and about 200° C., and at a reaction pressure between about 14 psi and about 2000 psi; and further comprising a step of introducing any iridium compound capable of dissolving in the acid medium under said temperature and pressure to generate the iridium catalyst.

19. The process of claim 16 further comprising a step of preparing the iridium catalyst from an iridium compound of the formula $IrX_3 \cdot nH_2O$ wherein n is any number between 0 and about 10, and X is an anion selected from the group consisting of fluoride, chloride, bromide and iodide.

20. The process of claim 16 further comprising a step of preparing the iridium catalyst from an iridium compound of the formula $IrX(CO)_yL_z$ wherein L is a neutral ligand selected from the group consisting of triphenylphosphine, pyridine, methylpyridine, aniline, and toluidine, and wherein y+z=2 or 3, and X is an anion selected from the group consisting of fluoride, chloride, bromide, iodide, formate, acetate, propionate, carbonate, nitrate, phosphate, sulfate, trifluoroacetate, cyclopentadienide, and pentamethylcyclopentadienide.

21. The process of claim 1 further comprising
   (a) preparing a mixture of terephthalic and isophthalic acids from the toluic acid; and
   (b) preparing a polyester from the mixture of terephthalic and isophthalic acids.

22. The process of claim 11 further comprising
   (a) preparing a mixture of terephthalic and isophthalic acids from the toluic acid; and
   (b) preparing a polyester from the mixture of terephthalic and isophthalic acids.

23. The process of claim 16 further comprising
   (a) preparing a mixture of terephthalic and isophthalic acids from the toluic acid; and
   (b) preparing a polyester from the mixture of terephthalic and isophthalic acids.

* * * * *